(12) United States Patent
Kucklick

(10) Patent No.: US 9,204,786 B2
(45) Date of Patent: Dec. 8, 2015

(54) RIGID ARTHROSCOPE SYSTEM

(71) Applicant: Cannuflow, Inc., San Jose, CA (US)

(72) Inventor: Theodore R. Kucklick, San Jose, CA (US)

(73) Assignee: Cannuflow, Inc., Campbell, CA (US)

( * ) Notice: Subject to any disclaimer, the term of this patent is extended or adjusted under 35 U.S.C. 154(b) by 0 days.

(21) Appl. No.: 14/526,285

(22) Filed: Oct. 28, 2014

(65) Prior Publication Data
US 2015/0112140 A1  Apr. 23, 2015

Related U.S. Application Data

(63) Continuation of application No. 13/557,040, filed on Jul. 24, 2012, now Pat. No. 8,870,748, which is a continuation of application No. 11/774,586, filed on Jul. 7, 2007, now Pat. No. 8,226,548.

(51) Int. Cl.
| *A61B 1/015* | (2006.01) |
| --- | --- |
| *A61B 1/00* | (2006.01) |
| *A61B 1/317* | (2006.01) |
| *A61B 17/34* | (2006.01) |
| *A61B 17/00* | (2006.01) |
| *A61B 19/00* | (2006.01) |

(52) U.S. Cl.
CPC ......... *A61B 1/00135* (2013.01); *A61B 1/00073* (2013.01); *A61B 1/00078* (2013.01); *A61B 1/015* (2013.01); *A61B 1/317* (2013.01); *A61B 17/3417* (2013.01); *A61B 17/3421* (2013.01); *A61B 17/3474* (2013.01); *A61B 2017/00092* (2013.01); *A61B 2019/465* (2013.01); *A61B 2217/007* (2013.01)

(58) Field of Classification Search
CPC ........... A61B 1/00073; A61B 1/00075; A61B 1/00135; A61B 1/00154; A61B 1/3132; A61B 1/317; A61B 2017/349; A61B 2017/00336; A61B 2217/007; A61B 2217/005; A61M 25/0043; A61M 25/02; A61M 25/04; A61M 1/0084; A61M 25/0662
See application file for complete search history.

(56) References Cited

U.S. PATENT DOCUMENTS

| 4,717,379 A | 1/1988 | Ekholmer |
| 4,973,321 A | 11/1990 | Michelson |
| 5,037,386 A | 8/1991 | Marcus et al. |
| 5,156,142 A | 10/1992 | Anapliotis et al. |
| 5,339,800 A | 8/1994 | Wiita et al. |
| 5,353,783 A | 10/1994 | Nakao et al. |
| 5,575,756 A | 11/1996 | Karasawa et al. |

(Continued)

FOREIGN PATENT DOCUMENTS

| JP | 07289499 | 11/1995 |
| JP | 09173281 | 7/1997 |

(Continued)

*Primary Examiner* — John P Leubecker
(74) *Attorney, Agent, or Firm* — K. David Crockett, Esq.; Susan L. Crockett, Esq.; Crockett & Crockett, PC

(57) ABSTRACT

A reinforced arthroscope comprising external ribs to provide for a number of separate fluid channels, such as inflow, outflow and interstitial tissue drainage, when the arthroscope is slipped into a disposable external sheath. The arthroscope is constructed to be sufficiently rigid so as to penetrate and move within a joint without damaging the rod optics inside. The externality of the arthroscope channels allow for cleaning and sterilizing the scope between uses.

3 Claims, 4 Drawing Sheets

(56) References Cited

U.S. PATENT DOCUMENTS

| | | |
|---|---|---|
| 5,601,603 A | 2/1997 | Illi |
| 5,637,075 A | 6/1997 | Kikawada |
| 5,762,604 A | 6/1998 | Kieturakis |
| 5,797,882 A | 8/1998 | Purdy et al. |
| 5,944,654 A | 8/1999 | Crawford |
| 6,117,070 A | 9/2000 | Akiba |
| 6,352,531 B1 | 3/2002 | O'Connor et al. |
| 6,354,992 B1 | 3/2002 | Kato |
| 6,616,600 B2 | 9/2003 | Pauker |
| 6,890,295 B2 | 5/2005 | Michels et al. |
| 7,150,713 B2 | 12/2006 | Shener et al. |
| 7,413,542 B2 | 8/2008 | Kucklick et al. |
| 7,445,596 B2 | 11/2008 | Kucklick et al. |
| 7,500,947 B2 | 3/2009 | Kucklick et al. |
| 2002/0069893 A1 | 6/2002 | Kawazoe |
| 2003/0004400 A1 | 1/2003 | Smith |
| 2003/0018340 A1 | 1/2003 | Branch |
| 2003/0130565 A1 | 7/2003 | Muller |
| 2005/0070759 A1 | 3/2005 | Armstrong |
| 2005/0085695 A1 | 4/2005 | Shener et al. |
| 2005/0171470 A1 | 8/2005 | Kucklick et al. |
| 2005/0192532 A1 | 9/2005 | Kucklick et al. |
| 2005/0203341 A1 | 9/2005 | Welker et al. |
| 2005/0203342 A1 | 9/2005 | Kucklick et al. |
| 2005/0234298 A1 | 10/2005 | Kucklick et al. |
| 2006/0041186 A1 | 2/2006 | Vancaillie |
| 2007/0060913 A1 | 3/2007 | Kucklick |
| 2007/0060915 A1 | 3/2007 | Kucklick |
| 2007/0185380 A1 | 8/2007 | Kucklick |

FOREIGN PATENT DOCUMENTS

| | | |
|---|---|---|
| JP | H1147080 | 2/1999 |
| JP | 2000503248 | 3/2000 |
| JP | 2007508871 | 4/2007 |
| WO | WO2007024662 | 3/2007 |
| WO | WO2007092662 | 8/2007 |
| WO | WO2007136729 | 11/2007 |

RIGID ARTHROSCOPE SYSTEM

This application is a continuation of U.S. application Ser. No. 13/557,040 filed Jul. 24, 2012, now U.S. Pat. No. 8,870,748, which is a continuation of U.S. application Ser. No. 11/774,586 filed Jul. 7, 2007, now U.S. Pat. No. 8,226,548.

FIELD OF THE INVENTIONS

The inventions described below relate to the field of arthroscopic surgical instruments.

BACKGROUND OF THE INVENTIONS

Arthroscopic surgery involves using optical instruments, such as an arthroscope, to visualize an operating field inside or near a joint of a patient. The same instrument or other instruments may be used to perform a surgical procedure in the operating field. Common instruments used in addition to the arthroscope include a trimming instrument for cutting tissue and an irrigation instrument for irrigating the surgical field. Each of the instruments requires its own incision to be introduced into the surgical field. Thus, many surgeons prefer to use only a trimming instrument and an arthroscope during arthroscopic surgical procedures.

Arthroscopes are fragile in relation to the forces applied during arthroscopic surgery, so a rigid cannula is placed over the arthroscope to reinforce it. The distal end of the rigid cannula is pointed, usually sharp, and thus the rigid cannula can scratch or gouge soft tissue within the operating field. The rigid cannula can also become stuck between bones or cartilage during a procedure. The metal surface of the rigid cannula can also damage metal prosthetics used to replace joints, resulting in a shortening of the useful life of the prosthetic and forcing the patient to undergo additional, painful surgeries to correct the problem.

An additional problem associated with arthroscopic surgery is maintaining a clear surgical field during surgery. Blood and debris can cloud the field, impairing a surgeon's ability to visualize tissue. One method of solving this problem is to use the irrigation instrument to clear the surgical field with saline. However, many surgeons strongly prefer to avoid the additional trauma caused by inserting a third instrument.

Known inflow and outflow endoscope systems introduce an irrigating fluid into the surgical site, thus obviating the need for a third instrument. For this purpose, the endoscope has an inflow channel defined by the inner surface of the sheath. The fluid passes through the channel and exits the distal end of the sheath to irrigate the operative site. Fluid at the surgical site may be withdrawn through an outflow channel defined by the outer surface of the inner sheath and the inner surface of a surrounding outer sheath. The outflow channel originates at the distal end of the instrument and transports fluid to an exit point at the proximal end of the outer sheath. The larger diameter of these systems requires larger and more traumatic surgical portals.

In arthroscopic surgery, as well as other surgical procedures, there remains a significant need for improved techniques that reduce the size of the portals while providing substantially continuous and properly managed fluid inflow and outflow. The Applicant's co-pending application Kucklick, Atraumatic Arthroscopic Instrument Sheath, U.S. application Ser. No. 11/094,626 filed (Mar. 29, 2005) describes an inflow/outflow sheath that reduces the diameter of the continuous flow system while properly managing surgical site fluid inflow and outflow. The inflow/outflow sheath is a tube having inwardly extending ribs that form multiple lumens when an arthroscope is inserted. The proximal portion of the sheath is provided with fluid ports, a manifold and other means of controlling the flow of fluid inside the sheath. The distal portion of the inflow/outflow sheath is provided with a plurality of holes. Each hole communicates with one or more of the lumens inside the tube, thereby allowing fluid to flow between the surgical field and sources or sinks located outside the patient. The inflow/outflow sheath thereby allows the surgeon to maintain a clear surgical field and protect the patient from accidental injury while eliminating the need for a third irrigation instrument.

Many surgeons use the endoscope not only for visualizing the surgical site, but also for manipulating the area in surgery. Excessive force on the sheathed endoscope may crush or shear off the plastic ribs on the inner side of the sheath, thus destroying the fluid channels. Excessive force can also break the scope, requiring very expensive repairs or replacement of the scope.

SUMMARY

The arthroscope described herein is reinforced, and has external ribs to provide for a number of separate fluid channels, such as inflow, outflow and interstitial tissue drainage. The arthroscope is constructed to be sufficiently rigid so as to penetrate and move within a joint and withstand high levels of torque and bending stress and thereby avoid damaging the rod optics inside (as is common in the typical use of un-reinforced arthroscopes). The externality of the arthroscope channels allow for cleaning and sterilizing the scope between uses.

The external sheath completes the fluid channels, and is made of a relatively simple polymer sheath to conform and seal to the external channel system on the structural arthroscope. The sheath is disposable and helps protect the joint tissue from unnecessary instrument trauma and scuffing. The external sheath is non-structural, relative to the arthroscope, and provides no substantial measure of rigidity to the assembled arthroscope and external sheath assembly. The sheath may also contain an instrument introduction port to allow the user to insert medical instruments into the surgical site through the fluid channels.

This arthroscope architecture gives the surgeon the "feel" of a traditional metal instrument, while providing for multiple fluid management channels in a low-profile, small diameter system. The additional rigidity of the scope helps to provide the tactile feedback the surgeon requires to know when a joint capsule has been entered and its position in the joint.

Further, the system may have permanently mounted sensors on the arthroscope such as for temperature and pressure. The temperature sensor may be of a class of sensors such as thermocouples, thermistors, or optical temperature sensors. The pressure sensors may be MEMS or surface-mounted electronic devices that operate in the range from 5-200 mm/Hg pressure, and are sterilizable.

DETAILED DESCRIPTION OF THE INVENTIONS

Figure 1:
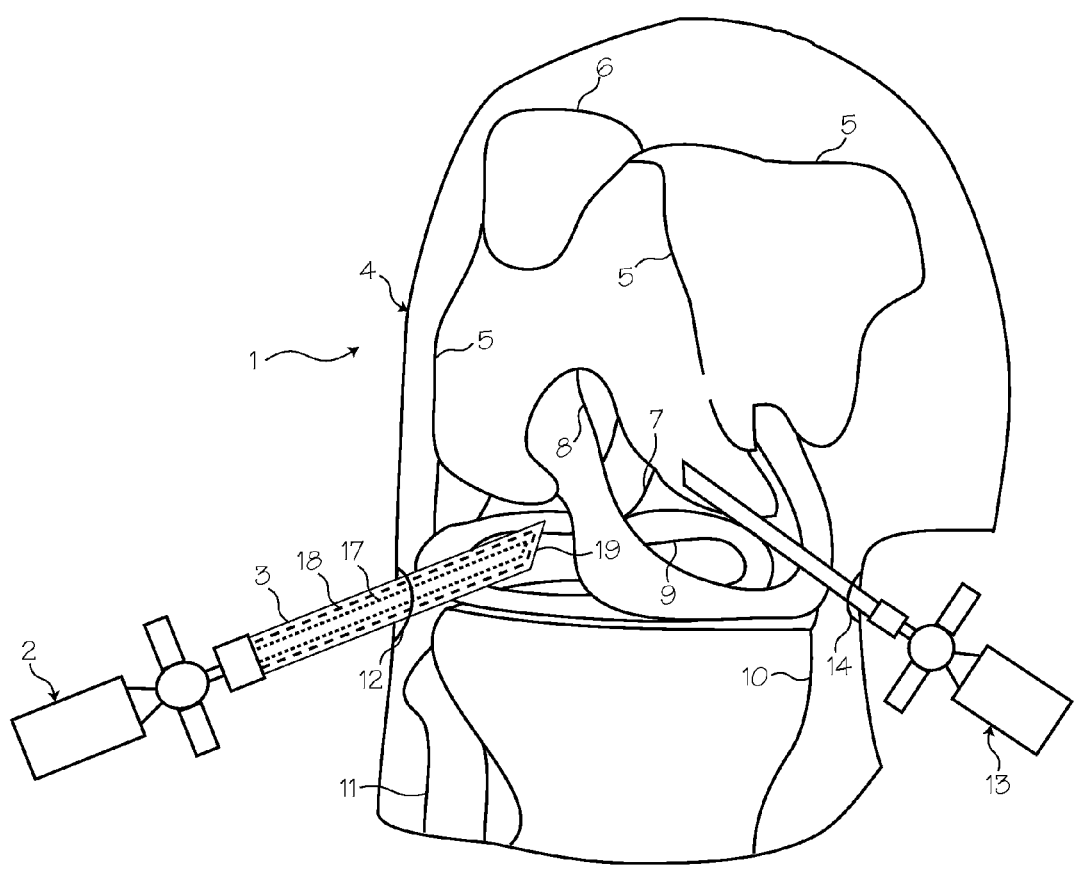
FIG. 1 shows a method of performing arthroscopic surgery on a patient.

FIG. 1 shows a method of performing arthroscopic surgery on a patient 1 using an arthroscope 2 sheathed in an atraumatic sheath 3. In FIG. 1, the various parts of the arthroscope are shown in phantom to indicate their positions inside the sheath. Various anatomical landmarks in the patient's knee 4 are shown for reference, including the femur 5, patella 6, posterior cruciate ligament 7, anterior cruciate ligament 8, meniscus 9, tibia 10 and fibula 11. During surgery, the surgeon introduces the arthroscope 2 into the knee via a first incision 12 in order to visualize the surgical field. A trimming instrument 13 is introduced through a second incision 14 to remove or trim tissue that the surgeon determines should be removed or trimmed.

The arthroscope 2 is an optical instrument comprising an optical rod 17 surrounded by a rigid tube 18. To protect the patient from unintended injury or trauma during the procedure, the arthroscope has been inserted into a resilient, outer introducer sheath or atraumatic sheath 3 that extends over the rigid tube 18.

Figure 2:
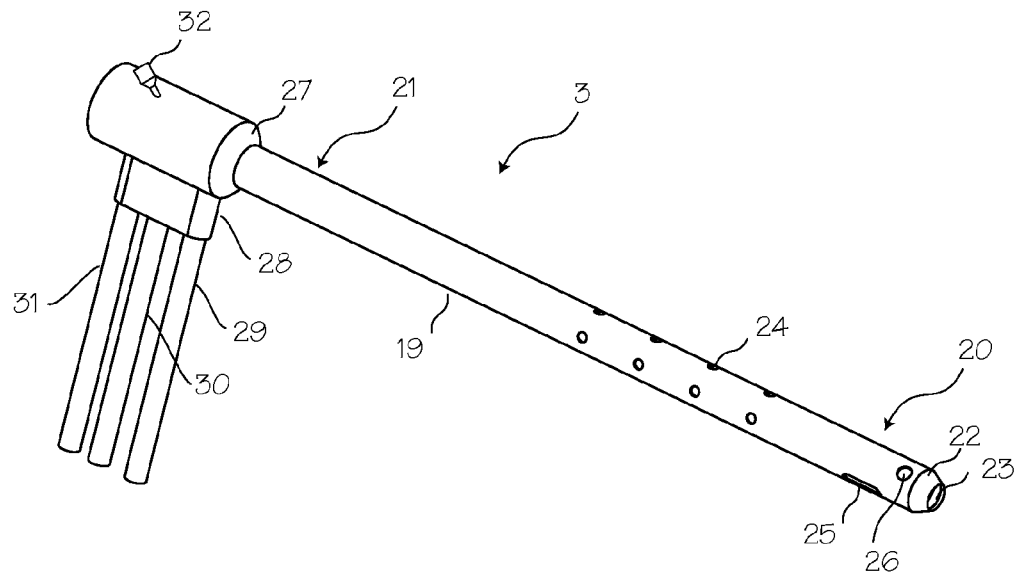
FIG. 2 shows the atraumatic sheath for use with the arthroscope of FIG. 3.

FIG. 2 illustrates the atraumatic sheath 3. The atraumatic sheath 3 is a tube 19 made of a disposable polymer or disposable metal, characterized by a central lumen. The external sheath is structurally less rigid than the metal arthroscope. The inner diameter of the atraumatic sheath is sized and dimensioned to closely fit over the outer diameter of an arthroscope. The tube 19 is characterized by a distal section 20 and a proximal section 21. The distal tip 22 of the atraumatic sheath is provided with a frusto-conical shape and an opening 23 that is slightly smaller in diameter than the outer diameter of the distal tip of the arthroscope. Alternatively, the tip may have an arcuate longitudinal cross-section. The opening 23 is provided in the atraumatic sheath so the surgeon may insert the tip of the arthroscope 2 through the opening and into the surgical space.

The distal section 20 of the sheath further comprises holes or apertures 24 for interstitial tissue drainage, apertures 25 for fluid aspiration, and apertures 26 for fluid irrigation. The proximal section of the atraumatic sheath is provided with a hub 27 manufactured from an elastomer to allow medical personnel to easily pull the atraumatic sheath over and secure the sheath to the arthroscope 2, thus creating a seal to establish the fluid flow channels. Further, the hub 27 can be adapted for coupling to a multi-channel irrigation and aspiration manifold 28. The fluid manifold is operably connected to the external sheath, and includes a plurality of fluid pathways communicating with the fluid channels defined by the sheath and ribs of the arthroscope. The manifold includes several conduits 29, 30 and 31 for connection of a source of irrigation fluid through the manifold to the irrigation fluid channels and corresponding apertures 26 at the distal tip of the sheath, connection of a vacuum source through the manifold to the aspiration channels and corresponding apertures 25 at the distal tip of the sheath, and connection of a vacuum source through the manifold to the interstitial tissue drainage channels and corresponding apertures 24 on the distal segment (proximal of the distal tip) of the sheath). Optionally, the hub further comprises an instrument introduction port 32. The port provides the user with the ability to pass instruments into the surgical site through the fluid channels described in detail below.

Figure 3:
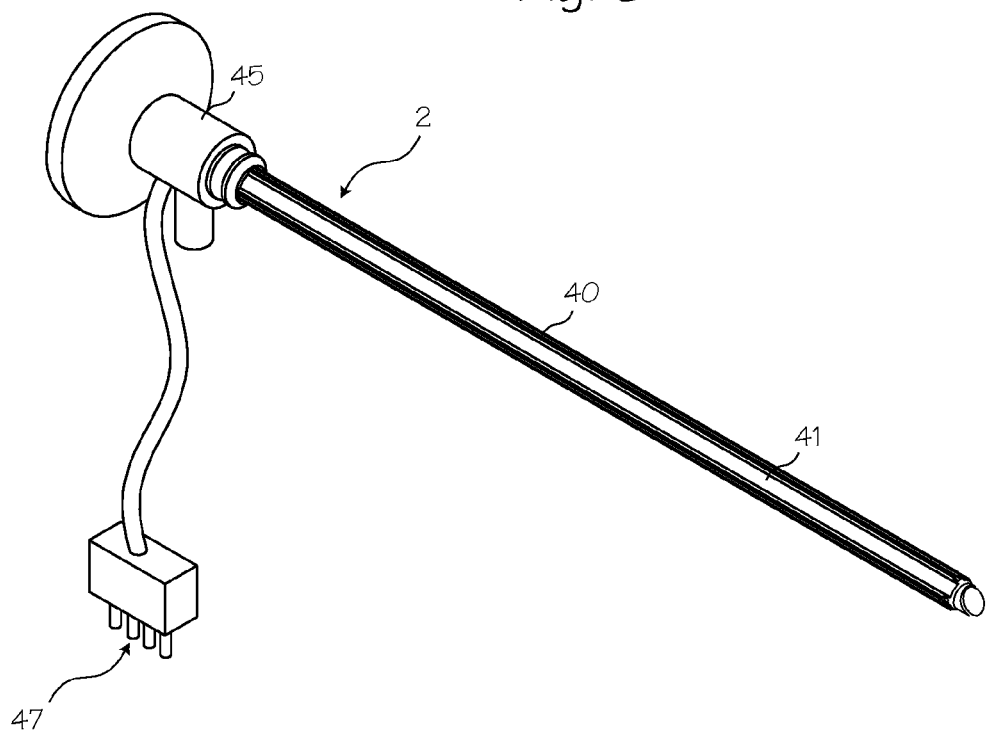
FIG. 3 shows the arthroscope with external ribs extending longitudinally along the length of the arthroscope.
Figure 5:
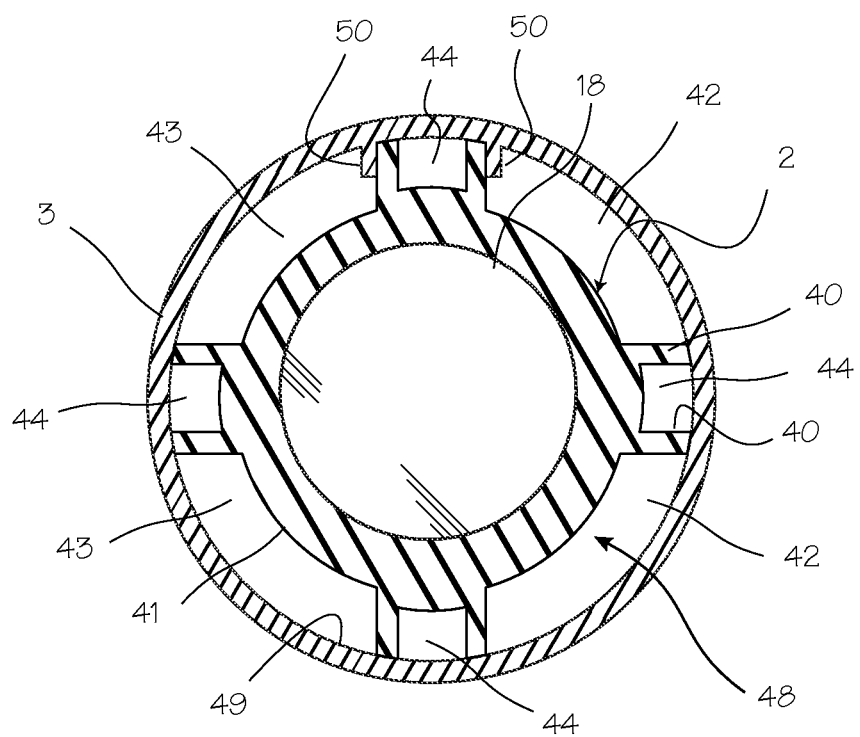
FIG. 5 shows a cross section of the distal portion of the assembled rigid arthroscope system.

FIG. 3 illustrates the arthroscope 2. The arthroscope is reinforced and has external ribs 40 extending longitudinally along the length of the arthroscope. The external ribs 40 extend radially from and run longitudinally along the outer surface 41 of the arthroscope 2. The ribs 40 form a seal with the inner surface of the sheath, thereby creating fluid channels (items 42, 43 and 44 shown in FIG. 5). The ribs provide for a number of separate fluid channels when the sheath is slipped over the arthroscope (as illustrated in FIG. 5). The arthroscope is releasably mounted to the base 45 such that the scope may be sterilized and reused for a number of surgical procedures.

Figure 4A:
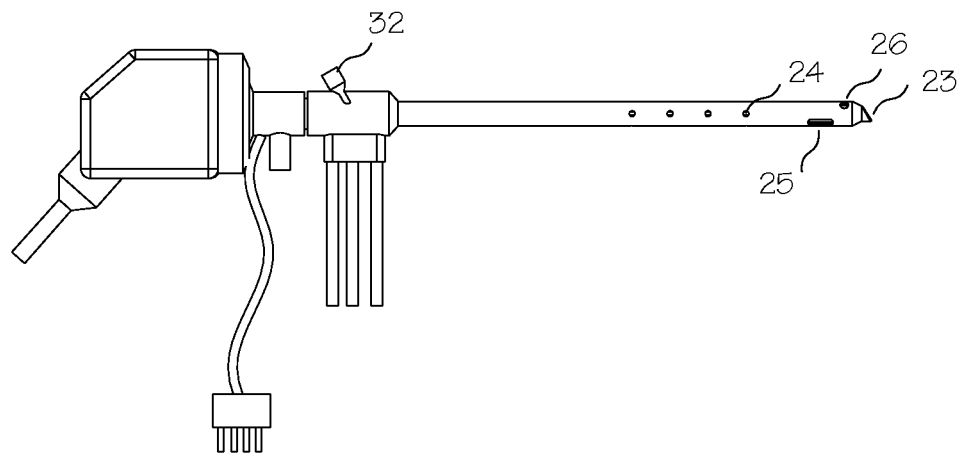
FIGS. 4a and 4b show the rigid arthroscope system, with the atraumatic sheath disposed over the arthroscope.
Figure 4B:
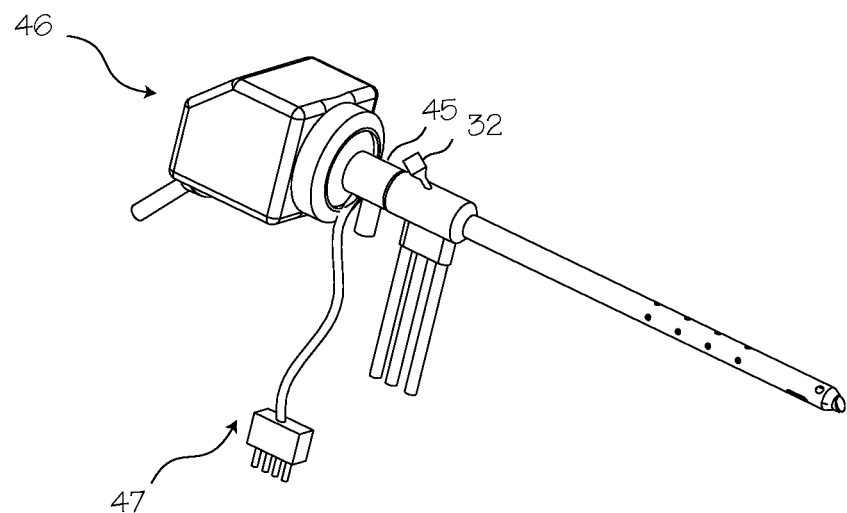

FIGS. 4a and 4b show the rigid arthroscope system wherein the atraumatic sheath 3 is slipped onto the arthroscope 2, and wherein the tip of the arthroscope extends distally from the tip 20 of the sheath 3. A camera 46 is operably connected to the base 45 of the arthroscope. Electronic sensors, such as temperature sensor or pressure sensors are mounted in the arthroscope. The temperature sensor may be of a class of sensors such as thermocouples, thermistors, or optical temperature sensors. The pressure sensors may be MEMS or surface-mounted electronic devices that operate in the range from 5-200 mm/Hg pressure, and are sterilizable. A sensor data interface 47 is functionally attached to the base 45 and interfaces with an external computer.

FIG. 5 illustrates a cross-sectional view of the arthroscope 2 and the atraumatic sheath 3 when assembled together. The arthroscope 2 is inserted into the sheath 3 through the central lumen 48. When the arthroscope and sheath are assembled, the inner surface 49 of the sheath comes in contact with the ribs 40 of the arthroscope 2. The force of the arthroscope ribs pushing against the inner surface of the sheath forms a seal between the ribs and the inner surface of the sheath 38. As shown, two irrigation channels 42, two aspiration channels 43, and four interstitial tissue drainage channels 44 are created by the ribs on the outer surface of the arthroscope 41 and the inner surface 49 of the inflow/outflow sheath when the sheath is slipped over the arthroscope. The lumens 42, 43, and 44 facilitate the substantially continuous inflow and outflow of fluids to and from a surgical site through the holes 24, 25 and 26 in the sheath. Radially and inwardly extending ribs or projections 50 on the inner surface of the sheath fits closely on either side of one or more ribs on the arthroscope to lock the sheath in place circumferentially relative to the arthroscope. Check valves or gates may also be coupled to the inner surface 49 of the inflow/outflow sheath within the lumens 42, 43, and 44 to prevent outflow fluids from flowing back towards the surgical site and to prevent inflow fluids from flowing out the proximal end of the sheath.

The ribs may be integrally formed on the arthroscopic instrument, as described above, or the ribs may be placed on a separate and additional rigid sheath to be placed over the arthroscope 2. In use, the separate rigid sheath comprising the ribs would be slipped onto the arthroscope 2 and the disposable sheath 3 would be slipped onto the separate rigid sheath, thus forming the fluid channels in a similar manner as described above. This would allow arthroscopes already in the field to be retrofitted with the new fluid channel technology described herein.

In use, a surgeon inserts the arthroscope into the sheath 3. The distal tip 22 expands as the distal end of the arthroscope 2 slides past the distal tip of the sheath. Because the inner diameter of the tip 23 is less than the outer diameter of the arthroscope 2, the tip will form a seal with the outer surface of the arthroscope 2. The Applicant's sheathed arthroscope can facilitate the substantially simultaneous flow of fluids to and from a surgical site through the lumens 42, 43 and 44 while requiring a smaller size incision. Substantially simultaneous inflow and outflow allows the surgeon to keep the surgical site clean and the field of view clear.

Medical instruments may be inserted into the instrument introduction port 32 and passed through any of the fluid channels 42, 43 and 44. These instruments may include RF or laser ablation devices, graspers, sutures, suture passers, suture anchors, suture needles, and diagnostic devices such as nerve stimulators.

The arthroscope is constructed to be sufficiently rigid so as to penetrate and move within a joint without damaging the rod optics inside. The externality of the channels allow for cleaning and sterilizing the scope between uses. The rigidity of the scope helps to provide the tactile feedback the surgeon requires to know when a joint capsule has been entered and their position in the joint. This arthroscope architecture gives the surgeon the "feel" of a traditional metal instrument, while providing for multiple fluid management channels, in a low-profile (diameter) system. It also ensures that the delicate optics survive the higher level of twisting and prying.

The word arthroscope used herein includes a family of instruments, including endoscopes, laparoscopes and other scopes. The scopes may use rod optics, fiber optics, distally mounted CCD chips, or other optical systems. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. An arthroscope system comprising:
   an arthroscope comprising a plurality of external ribs extending radially from and running longitudinally along the outer surface of the arthroscope, said external ribs integrally formed on the outer surface of the arthroscope;
   an external sheath having an inner surface and a central lumen, said sheath characterized by a central portion;
   wherein the external sheath has an internal diameter closely matching the external diameter of the arthroscope whereby the inner surface of the external sheath, in conjunction with the ribs, define a plurality of fluid channels longitudinally extending within the arthroscope system; and
   apertures disposed on the central portion of the sheath in fluid communication with the fluid channels;
   said system further comprising a temperature sensor operably connected to the arthroscope, a pressure sensor operably connected to the arthroscope, and a sensor data interface operably connected to the arthroscope.

2. The arthroscope system of claim 1 further comprising:
   a fluid manifold operably connected to the external sheath, said manifold comprising a plurality of fluid pathways communicating with the plurality of fluid channels;
   a source of irrigation fluid operably connected to the manifold and at least one of the fluid channels;
   a vacuum source operably connected to the manifold and at least one of the fluid channels.

3. The arthroscope of claim 1, wherein the external sheath further comprises an instrument introduction port operably connected to the sheath to allow instruments to pass through the fluid channels.

\* \* \* \* \*